United States Patent [19]

Stevens et al.

[11] Patent Number: 5,543,018
[45] Date of Patent: Aug. 6, 1996

[54] METHOD AND APPARATUS FOR AUTOMATED ELECTROPHORESIS USING LIGHT POLARIZATION DETECTOR

[75] Inventors: John K. Stevens; Alexandre M. Ismailov, both of Toronto, Canada

[73] Assignee: Visible Genetics Inc., Toronto, Canada

[21] Appl. No.: 387,272

[22] Filed: Feb. 13, 1995

[51] Int. Cl.$^6$ .......................... G01N 27/26; G01N 27/447
[52] U.S. Cl. .......................... 204/461; 204/467; 204/612; 204/618; 356/344
[58] Field of Search .......................... 204/299R, 182.8; 356/364, 366, 367, 368, 370, 344

[56] References Cited

U.S. PATENT DOCUMENTS

| | | | |
|---|---|---|---|
| 4,498,774 | 2/1985 | Yeung et al. | 356/368 |
| 4,811,218 | 3/1989 | Hunkapiller et al. | 364/413.01 |
| 4,881,812 | 11/1989 | Ohkubo et al. | 356/344 |
| 4,902,134 | 2/1990 | Spanier | 356/364 |
| 4,930,893 | 6/1990 | Manian | 356/344 |
| 5,012,101 | 4/1991 | Goodall et al. | 356/366 X |
| 5,062,942 | 11/1991 | Kambara et al. | 204/299 R |
| 5,091,652 | 2/1992 | Mathies et al. | 250/458.1 |
| 5,108,179 | 4/1992 | Myers | 356/344 |
| 5,122,345 | 6/1992 | Tabor et al. | 422/116 |
| 5,162,654 | 11/1992 | Kotichka et al. | 250/458.1 |
| 5,168,326 | 12/1992 | Tokieda et al. | 356/368 |
| 5,190,632 | 3/1993 | Fujimiya et al. | 204/299 R |
| 5,192,412 | 3/1993 | Kambara et al. | 204/299 R |
| 5,207,880 | 5/1993 | Middendorf et al. | 204/182.8 |
| 5,213,673 | 5/1993 | Fujimiya et al. | 204/299 R |
| 5,230,781 | 7/1993 | Middendorf et al. | 204/182.8 |
| 5,242,567 | 9/1993 | Fujimiya et al. | 204/299 R |
| 5,290,419 | 3/1994 | Kambara et al. | 204/299 R |
| 5,294,323 | 3/1994 | Togusari et al. | 204/299 R |
| 5,307,148 | 4/1994 | Kambara et al. | 356/344 |
| 5,314,602 | 5/1994 | Kambara et al. | 204/299 R |
| 5,324,401 | 6/1994 | Yeung et al. | 204/180.1 |
| 5,360,523 | 11/1994 | Middendorf et al. | 204/182.8 |
| 5,365,455 | 11/1994 | Tibbetts et al. | 364/497 |

OTHER PUBLICATIONS

Atsushi Yamamoto et al "Polarized Photometric Detector for High–Performance Liquid Chromatography" Analytical Sciences (Oct. 1991).

Atsushi Yamamoto et al "Enantiomeric purity determination by high–performance liquid chromatography with coupled polarized photometric/UV detection. Analysis of aduterative addition of synthetic malic and tartaric acids" Journal of Chromatography A (1994) 85–89.

Minren Xu and Chieu D. Tran, "Thermalkeus–Circular Diehroism Detector for High–Performance Liquid Chromatography" Analytical Chemistry, Vol. 62, No. 22 (Nov. 15, 1990).

(List continued on next page.)

Primary Examiner—John Niebling
Assistant Examiner—John S. Starsiak, Jr.
Attorney, Agent, or Firm—Oppedahl & Larson

[57] ABSTRACT

Changes in polarized light incident on a detection zone within a separation matrix are used to detect optically active molecules within the separation matrix. The separation and detection of optically active molecules within the detection zone is done by loading a sample containing optically active molecules onto a separation matrix; applying a motive force to cause the sample to migrate through the separation matrix and to separate into a plurality of subgroups of optically active molecules; directing an incident beam of polarized radiation to the detection zone; processing the collected exiting beam with an optical component which discriminates between radiation having the same polarization as the incident beam and radiation having a different polarization from the incident beam; and measuring the intensity of the processed exiting beam. A difference between the intensity of the processed exiting beam and a standard intensity obtained for the separation matrix in the absence of sample is indicative of the presence of an optically active molecule in the detection zone. Alternatively, an incident beam of alternately left and right circularly polarized radiation, in which case differences in the intensity of left and right circularly polarized radiation indicate the present of optically active species within the detection zone.

43 Claims, 5 Drawing Sheets

OTHER PUBLICATIONS

Stephen F. Mason et al, "Simultaneous Monitoring of Light Absorption and Optical Activity in the Liquid Chromatography of Chiral Substances" Journal of Chromatography 202 (1980) 239–245.

Edward S. Yeung et al, "Detector Based on Optical Activity for High Performance Liquid Chromatographic Detection of Trace Organics" Analytical Chemistry, Vol. 52, No. 9 (Aug. 1980) 1399–1402.

Van Holde, K. E., *Physical Biochemistry*, Chap. 10, pp. 202–218, Prentice Hall, Englewood Cliffs, NJ (1971).

Smith et al., "Flourescence detection in automated DNA sequence analysis," *Nature* 321: 674–679 (1986).

METHOD AND APPARATUS FOR AUTOMATED ELECTROPHORESIS USING LIGHT POLARIZATION DETECTOR

BACKGROUND OF THE INVENTION

This application relates to a method and apparatus for detecting optically active molecules such as proteins, nucleic acids or the like, after such molecules have separated within a separation matrix, using inherent properties of the molecules for their detection.

Separation of organic molecules is now routinely performed using many types of separation matrices and techniques such as in agarose or polyacrylamide gel electrophoresis. (Current Protocols in Molecular Biology (John Wiley & Sons, 1994)) A gel provides a suitably insoluble sieve so as to permit the separation of organic molecules in solution by size and conformation as they are drawn through the sieve under electromotive force. Such separation of organic molecules provides valuable insights into their structures and functions. For example, polyacrylamide gel electrophoresis (PAGE) separation can separate two polypeptides of the same size but of different isoforms or polypeptides only 100 daltons difference in size (Current Protocols, 1994, Chp. 10). Another use for PAGE is in separation of nucleic acids based on size of fragments, such as in the extremely important application of DNA sequence determination (Maniatis, "Molecular Cloning", A Laboratory Manual, 2nd ed., 1987).

When the electrophoresed molecules are labeled with a detectable signal, it is possible to detect the separations of molecules in real time. For example, nucleic acids conjugated with a fluorophore may be loaded at a first end of a polyacrylamide gel, separated under electrophoresis, and detected at a second end of the gel by laser induced fluorescence of the conjugated label. The fluorescence signal may be displayed as it is recorded or stored in a computer.

Since the first description of a real-time nucleic acid separation method and apparatus (Smith et al., Sequence Detection in Automated DNA Sequence Analysis, Nature 321: 674–679 (1986)) the technology for so-called "automated DNA sequencing" has expanded rapidly. Several automated DNA sequencing apparatuses are commercially available. Methods and apparatus for sequencing of DNA are described in U.S. Pat. Nos. 4,811,218; 4,881,812; 5,062,942; 5,091,652; 5,108,179; 5,122,345; 5,162,654; 5,171,534; 5,190,632; 5,207,880; 5,213,673; 5,230,781; 5,242,567; 5,290,419; 5,294,323; 5,307,148; 5,314,602; 5,324,401; and 5,360,523 which are incorporated herein by reference.

The means of detection of separated molecules is of fundamental technical significance in each electrophoresis system. As a general rule, most published methods of detection of electrophoresed DNA or protein samples rely on indirect detection of sample. For example, some methods rely on detection of fluorophore conjugated to the molecule of interest; other methods rely on detection of a radioactive label conjugated to the molecule of interest; still others rely on visualization of separated bands of molecules by staining of whole gels. All of these methods entail time-consuming, dangerous or cumbersome preparatory procedures for labeling the molecule of interest. For example, conjugation of a DNA sequencing primer to a fluorescein or rhodamine molecule requires use of a low efficiency conjugation reaction that leaves a large pool of unlabeled primers which reduce the efficiency of the DNA sequencing reactions, and interfere with the running of the gel.

To avoid the labeling problem, a method and apparatus are required to identify molecules based on inherent qualities of those molecules. One such method is disclosed in U.S. Pat. No. 4,930,893. This method makes use of a shearing interferometer to detect differences in the index of refraction between molecules to be analyzed and the surrounding medium. This method, however, utilizes complicated optical components, and is not shown to be useful for obtaining the real-time electrophoresis data which is important to the full implementation of genetic diagnostic and screening procedures.

It is an object of the present invention to provide an improved optical detection method for real time detection of optically active materials such as DNA or protein samples in an separation matrix based on detection of a property inherent to the DNA or protein sample.

It is a further object of the present invention to provide an apparatus for real time detection of optically active materials in a separation matrix which utilizes common optical components.

SUMMARY OF THE INVENTION

These and other objects of the invention are achieved using changes in polarized light incident on a detection zone with a separation matrix to detect optically active molecules within the separation matrix. Thus, in one embodiment of the invention, the invention provides a method for separating and detecting the presence of optically active molecules within a detection zone in a separation matrix comprising the steps of:

(a) loading a sample containing optically active molecules onto a separation matrix;

(b) applying a motive force to the sample to cause the sample to migrate through the separation matrix and to separate the sample into a plurality of subgroups of optically active molecules;

(c) directing an incident beam of polarized radiation to the detection zone of the separation matrix;

(d) processing an exiting beam of radiation which has passed through the detection zone of the separation matrix with an optical component which discriminates between radiation having the same polarization as the incident beam and radiation having a different polarization from the incident beam; and (e) measuring the intensity of the processed exiting beam, wherein a difference between the intensity of the processed exiting beam and a standard intensity obtained for the separation matrix in the absence of sample is indicative of the presence of an optically active molecule in the detection zone.

This method can be carried out using an apparatus containing very simple optical components. Thus, a basic apparatus in accordance with the invention comprises:

(a) a source of polarized radiation;

(b) a separation matrix disposed in a position such that a detection zone extending perpendicular to the direction of sample migration within the separation matrix is in the path of the polarized radiation;

(c) a filter or other optical component which discriminates between the polarized radiation which has passed through the separation matrix in the absence of the sample and polarized radiation which has passed through the separation matrix in the presence of optically active molecules from the sample; and (d) a detector for determining the intensity of the radiation which passes through the filter. Preferably, the apparatus of the invention also includes means for applying a motive force such as an electric field to the separation matrix.

An alternative embodiment makes use of an incident beam of alternately left and right circularly polarized radiation of the type generated using a Pockels cell or Ker cell. When such radiation encounters an optically active substance which absorbs radiation of the incident wavelength, radiation of one polarization is preferentially absorbed. Differences in the intensity of the pulses of left and right circularly polarized radiation that has passed through the detection zone of the separation matrix indicate the present of optically active species within the detection zone.

DETAILED DESCRIPTION OF THE INVENTION

This invention provides a method and apparatus for detecting and, if desired, collecting subpopulations of optically active molecules after they have separated within a separation matrix. The invention depends on the fact that optically active molecules shift the polarization of an input beam of polarized electromagnetic radiation in a detectable manner, and utilizes this fact to provide a method which can be used for the detection of unmodified molecules, particularly nucleic acid polymers, peptides and proteins, on a separation matrix.

Figure 1:
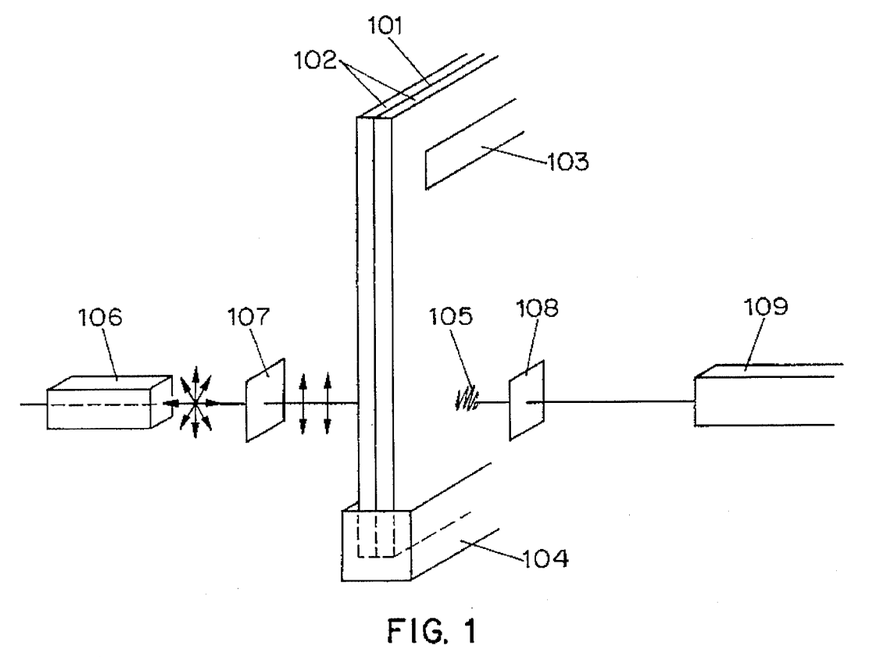
FIG. 1 shows an embodiment of the invention for separation of molecules on a vertical electrophoresis gel.

FIG. 1 illustrates the operation of one embodiment of the invention. As shown, a separation matrix 101 in the form of an electrophoresis gel is disposed between a radiation source 106 and a detector 109. Electrodes 102 and 104 create an electric field in the gel which acts as an electromotive force, causing electrically charged molecules, such as nucleic acid polymers, loaded at the loading site 103 to migrate towards electrode 104. Differently sized molecules will migrate towards electrode 104 at different rates because of their relative mobility differences in the gel. Subpopulations of the same size and charge will move as a single band through the gel. When sufficient separation of the bands has been obtained, these subpopulations may be detected as discrete populations in a detection zone 105 located within the separation matrix 101.

In FIG. 1, the radiation source 106 produces a beam of unpolarized radiation which is directed towards the detection zone 105. A first polarization filter 107 is placed between the radiation source 106 and the detection zone 105. The first polarization filter 107 allows transmission of radiation of only one polarization. Transmitted polarized radiation illuminates the detection zone in a spot of 0.03 mm to 0.3 mm diameter. The radiation passes through the separation matrix 101 and encounters a second polarization filter 108. If the radiation passes through the second polarization filter 108 it is detected by a detector 109.

An inherent feature of molecules such as nucleic acid polymers and proteins in solution is the ability of each molecule to rotate the plane of polarization of a radiation beam which passes through the solution. This characteristic is sometimes referred to as "optical activity." The direction of the rotation depends on the structure of the molecule, with any given structure and its mirror image isomer causing rotation in opposite directions.

A solution of equal numbers of each mirror image isomer would cause no detectable optical rotation of the radiation beam. However, the organic molecules produced by living systems and generally studied by researchers are uniquely of one stereoisomer and thus can be detected by the optical rotation of polarized radiation. Therefore the presence of nucleic acid or protein in the detection zone causes rotation of the radiation which is transmitted through the separation matrix and a shift in the polarization. Detection of this shift thus permits direct analysis of unmodified molecules within the separation matrix. This detection can be detected using either of three general approaches.

In the first approach, the second polarization filter 108 may be oriented such that it is in alignment with the first polarization filter 107, i.e., so that it transmits radiation of the same polarization as the first polarization filter 107. In this case, the detector 109 will receive radiation when there is no optically active material in the detection zone 105. When a band of optically active material is present in the detection zone, however, it causes the input radiation to be rotated, and thus not transmitted through the second polarization filter 108 to the detector 109. A reduction in detected radiation is recorded as a band of optically active material.

Alternatively, in the second approach, the second polarization filter 108 can be oriented out of alignment with the first polarization filter 107. In this case, the second polarization filter is positioned such that a band of optically active material will cause the rotation of radiation to an angle which is transmitted through the second polarization filter 108. An increase in the detected transmission of radiation is recorded as the presence of the optically active material.

An important aspect of the implementation of these two approaches is the proper selection of polarization filters. The polarization filter should permit only an extremely narrow range of polarizations to pass through it. This feature flows from the problem that small concentration of sample present at the detection zone will cause only a very slight amount of optical rotation (at least at concentrations of sample below about 175 mg/ml). In order for the detector to maintain a high signal to noise ratio, the slight amount of rotation of radiation must result in a substantial decrease of transmitted radiation, in the first approach described above, or in a substantially increase in transmitted signal being detected, in the second approach described above. Commercial polarization filters of high quality are available from companies such as Melles Griot, Edmund Scientific and Newport. In some cases, the preferred polarization filter will consist of two polarization filters slightly rotated with respect to each other, thus allowing only a narrow range of polarizations, common to both filters, to pass through the combined filter.

In addition to using high quality polarization filters where required, it is useful to employ other means to enhance the rotation of light by the sample. One such method is described in U.S. Pat. No. 4,902,134 which is incorporated herein by reference. In this method, optical rotation of signal is amplified by passing polarized light through a sample a plurality of times such that changes in the polarization state from the respective passes are cumulative. Appropriate positioning of mirrors and quarter wave compensators is required.

Another method of increasing optical rotation at the detection zone is to increase length of the gel cell at the detection zone or to use a higher concentration of sample. These results flow from the fact that optical rotation increases directly with increasing concentration of sample and with increasing length of the detection cell (using the same concentration of sample). Increasing the length of the detection cell is a less desirable method, for it requires an overall thicker electrophoresis gel which requires use of greater amounts of electric current to drive the electrophoresis. However, an effective doubling of the cell size can be achieved without this drawback by placing a reflective surface on the bottom of the separation matrix and collecting the exiting beam after reflection back through the detection zone.

One embodiment of the invention which is useful with some detectors employs elliptically polarized radiation as an input radiation source. The embodiment is designed similar to the design of FIG. 1. The fundamental difference is that the input radiation beam consists of radiation of two plane polarizations: a relatively intense major vector and a relatively less intense minor vector. In the absence of sample, the second polarization filter 108, permits only the transmission of light of the minor vector. The signal obtained by the detector 109 from the minor vector is used as a standard to normalize the background noise of the detector 109. When sample is present in the detection zone 105, the minor vector rotates far enough that it is no longer detected. However, the major vector is positioned such that the presence of sample will rotate the major vector to allow transmission of the major vector through the second polarization filter 108. In the presence of sample, therefore, the detector fails to identify the radiation of the minor vector, but is exposed to the more intense radiation of the major vector. An increase in radiation detected indicates the passing of an optically active molecule.

Figure 8:
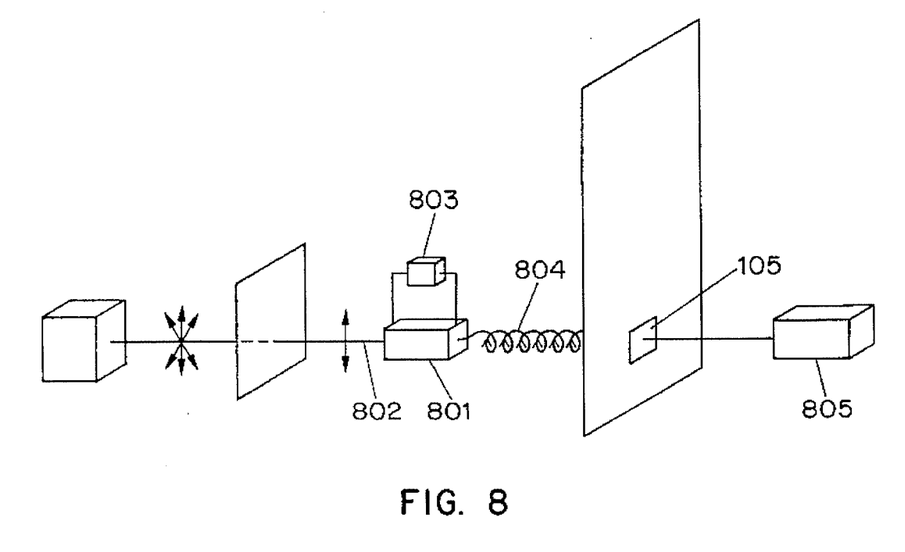
FIG. 8 shows an apparatus according to the invention using a circularly polarized incident beam.

In the third approach, illustrated in FIG. 8, all the processing of the incident radiation beam takes place upstream of the detection zone 105. The technique relies on the optical rotatory dispersion of optically active molecules, i.e, the fact that such molecules preferentially absorb either right or left circularly polarized radiation, rather than on the rotation of polarized light by the sample. In an apparatus implementing this approach, circularly polarized radiation may be produced using a Pockels Cell or Ker Cell 801. The incident beam of plane polarized light 802 is directed to a cell 801, which can be a Pockels cell (if liquid) or Ker cell (if crystal). The cell has an electric field, induced by a power supply 803, suspended across it. A proper density electric field causes the plane polarized beam to be emitted as a circularly polarized beam 804. By reversing the electric field of the cell, which period of reversal may have a period as brief as a few 10's of nanoseconds, a stream of alternating circularly polarized light is emitted by the cell 801. In the absence of optically active molecules at the detection zone 105, the exiting beam has a standard intensity, being composed of equal amounts of alternating circularly polarized light. However, when an optically active molecule is present at the detection zone 105, the molecule preferentially absorbs light of one circular polarity. A detector 805 positioned to receive the exiting beam will receive less light of the preferentially absorbed rotation when the optically active molecule is present at the detection zone 105. A preferential reduction of intensity of one half of the incident beam from the standard intensity produces an oscillatory output signal which indicates the presence of an optically active molecule in the detection zone.

As used herein, the term "separation matrix" refers to any insoluble sieve which can be used to for the separation of organic molecules in solution by size and conformation and which allows transmission of a detectable amount of electromagnetic radiation that responds to the chirality of the optically active molecules of interest. Suitable types of matrices include agarose, polyacrylamide (both with and without denaturing additives) and the like.

The separation matrix may be in essentially any form which can be used for the separation of the optically active molecules within the sample. Thus, for example, the separation matrix may be in the form of a chromatography column, in which case the motive force applied is gravity or a hydrostatic pressure caused by pumping liquid through the column. Preferably, however, the separation matrix is an electrophoresis gel for separation of the molecules of interest in response to an electromotive force.

Electrophoresis gels useful in the present invention includes gels of the type used in known automated nucleic acid sequencers, for example the 28 cm×35 cm×0.35 to 0.5 mm gels used in the Pharmacia A.L.F. sequencer. In addition, if sufficient concentrations of molecules are found in each band, then extremely thin gels (5–10 microns) such as those described in U.S. patent application Ser. No. 08/332, 557, which is incorporated herein by reference, or capillary electrophoresis apparatus may be used to separate molecules. Such extremely thin gels have the particular advantage that they can separate molecules quickly in an extremely high electric field density (100–1000 volts/cm) using relatively low amounts of energy.

The radiation source used in the present invention may be essentially any source which produces radiation of sufficient intensity to be detected after polarization and passage through the separation matrix with which it is used. For example, the radiation source may be a conventional lamp, such as a mercury vapor or xenon lamp, a laser, for example a helium-neon or argon ion laser, a light-emitting diode (LED) or other ultraviolet, visible, or infrared light source.

In the case of the detection of variations in the intensity of circularly polarized radiation, the incident radiation is selected to be of a wavelength which is absorbed by the substance of interest, i.e, proteins or nucleic acid polymers.

In the case of those embodiments where changes in polarization angle are observed, it will be understood by persons skilled in the art that optically active molecules rotate radiation to a greater extent at some wavelengths than at others. Thus, it may be advantageous to match the wavelength of the radiation source to a wavelength at which the specific molecule of interest has a high specific rotation in order to obtain the greatest sensitivity.

Proteins with different amino acid compositions often have substantially different wavelengths of maximum optical rotations. Such wavelengths may change depending on the secondary structure of the protein in solution. Nucleotide polymers also have different wavelengths of maximum optical depending on the monomers from which they are composed. Because of the complexity of these interaction, it will be appreciated that the best technique for determine the optimum wavelength to employ is by systematically testing a variety of wavelengths of input radiation, likely in the ultraviolet, visible or infra-red ranges, and observing which wavelength receives the exhibits the maximum amount of optical rotation in the particular system which the person is studying.

Persons skilled in the art will also recognize that other optical elements in place of the polarization filters 107 and 108 depicted in FIG. 1. For example, selection of a single polarization can be achieved using reflective element such as mirrors.

The detector 109 may be any type of detector which has sufficient sensitivity and accuracy to the radiation at the wavelength of the radiation source to discriminate between the signal obtained in the presence and absence of the optically active compound in the detection zone. Suitable types of detectors include photomultiplier tubes and photodiodes, particularly silicon photodiodes.

An embodiment of the invention suitable for running with ultrathin (2–10 micron) electrophoresis gels relies on the birefringent properties of DNA in a liquid crystal state. Ultrathin layers of liquid crystals are routinely employed in the liquid crystal display industry. In certain orientations, liquid crystals have birefringent properties that cause substantial rotation of light and cause easily detectable light effects. Adapting this methodology to detection of DNA, it is observed that DNA in liquid crystal state acts as a birefringent material that will cause a substantially greater rotation of light than would the same amount of molecules in dilute solution based on optical activity. Research has shown that DNA, like other semi-rigid polymers in high concentration, has a natural tendency to form a liquid crystal at approximately 250 mg/ml. (Strzelecka et al., "Multiple liquid crystal phases of DNA at high concentration", *Nature* 331:457–60 (1988); Rill R. L., "Liquid crystalline phase in concentrated aqueous solutions of Na+DNA", *Proc. Natl. Acad. Sci. USA* 83(2) 342–6 (1986).) This embodiment therefore relies on the principle that tiny amounts of DNA can be detected if they are in liquid crystal state at the detection zone.

Figure 9:
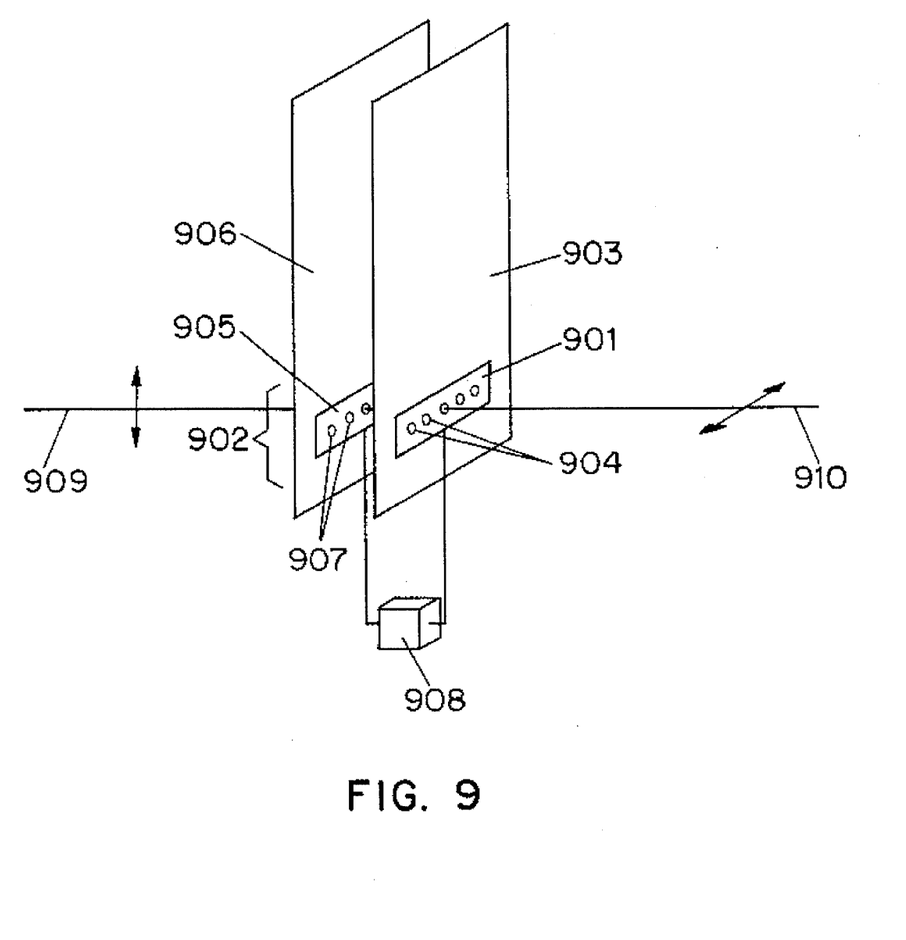
FIG. 9 shows an apparatus according to the invention which generates a localized high-intensity electric field in the detection zone.

In order to achieve the formation and organization of the liquid crystal at the detection zone it is necessary to adapt the electrophoresis apparatus to allow DNA to be concentrated to at least 250 mg/ml and/or be otherwise highly ordered at the detection zone. FIG. 9 illustrates a method wherein a localized high density pulsed electric field is employed to organize the DNA at the detection zone. A first electrode 901 is positioned at the detection zone 902 on a first substrate 903 of the gel holder, leaving small diameter openings 904 for the transmission of the radiation beam 909 at each particular detection zone. A second electrode 905 is positioned at the detection zone 902 on the second substrate 906 of the gel holder, again leaving small diameter openings 907 for the transmission of the radiation beam at each particular detection zone. A high density electric field pulse induced by a power supply 908 between the electrodes causes DNA to migrate towards the anode and to aggregate there in high concentration. The birefringent effect of the DNA liquid crystal causes a high degree of optical rotation of the exiting radiation 910. Using the polarization filters as described in FIG. 1, the optical rotation is detected by the detector 109. This embodiment may be enhanced by utilization of buffer solutions which improve the tendency of the DNA to form a liquid crystal at the detection zone. In order to achieve best results for liquid crystal formation, it may be necessary to temporarily turn off the primary electric field suspended across the entire electrophoresis gel while the localized high density pulsed electric field is engaged.

A preferred embodiment of the present invention is a method for determining the sequence of a nucleic acid polymer. The initial steps of such a procedure will be familiar to persons skilled in the art relating to sequencing. Essentially the process involves combining the nucleic acid polymers (optionally after amplification) with a sequencing primer; extending the sequencing primer in the presence of normal nucleotide (A, C, G, and T) and a chain-terminating nucleotide, such as a dideoxynucleotide, which prevents further extension of the primer once incorporated; and analyzing the product mixture (referred to in the specification and claims hereof as a "sequencing product mixture") for the length of the extended fragments obtained. In the case of the present invention, this analysis of fragments is done by electrophoresis, and the products are detected using an incident beam of polarized radiation, an optical element which discriminates between polarized radiation which is the same as the incident beam and polarized radiation which is different; and a detector.

The analysis of the fragments in accordance with the invention may be done after the completion of the electrophoresis by scanning the gel for areas in which optically active molecules are concentrated. Preferably, however, the fragments are analyzed in real time as the bands of material migrate through a defined detection zone near one end of the gel.

Though this invention is designed to detect inherent characteristics of optically active molecules, and thus avoid the cumbersome fluorescent labeling process of existing automated sequencers, there is a labeling method which may prove advantageous for some embodiments of this invention. The labeling method employs a rotation enhancer molecule which demonstrates a very high specific rotation, of the same direction of rotation as the subject optically active molecule, and by conjugation or other chemical linkage method, binds the subject optically active molecule with the rotation enhancer molecule. The rotation enhancer molecule can be any molecule which (a) demonstrates a high degree of optical activity of the same direction as the subject optically active molecule; (b) does not convert to its isomeric racemate during the time period of use; (c) can be effectively conjugated or otherwise linked to the subject optically active molecule; and (d) does not detrimentally interfere with the electrophoresis of the subject optically active molecule.

Figure 2:
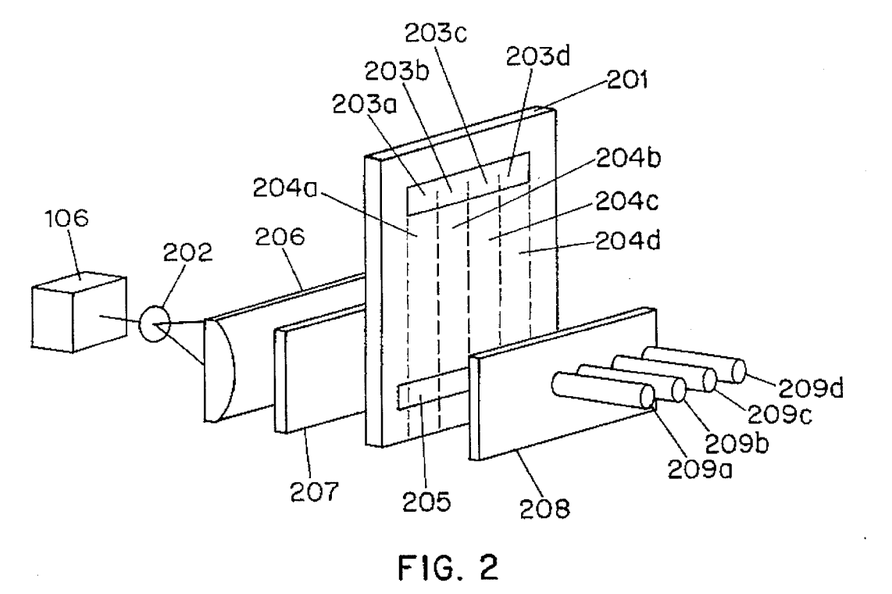
FIG. 2 shows a further embodiment of the invention useful in real-time sequencing of nucleic acid polymers.

FIG. 2 shows an embodiment of the invention suitable for a real-time nucleic acid sequencing procedure. In this case, four different sequencing product mixtures (one for each type of dideoxynucleotide) are loaded onto four loading sites 203*a*, 203*b* 203*c* and 203*d* of an electrophoresis gel 201. Of course, more than four loading sites will frequently be included on a single gel, and the use of four lanes in this illustration in no way limits the scope of the invention.

An electric field is applied to the gel using electrodes (not shown) causing the four samples mixtures to migrate and separate within parallel lanes 204*a*, 204*b*, 204*c* and 204*d*. The polarized incident radiation beam is delivered an elongated detection zone 205 extending across the lower end of each of the lanes, and detected using an array of detectors 209*a*, 209*b*, 209*c* and 209*d*.

Figure 3:
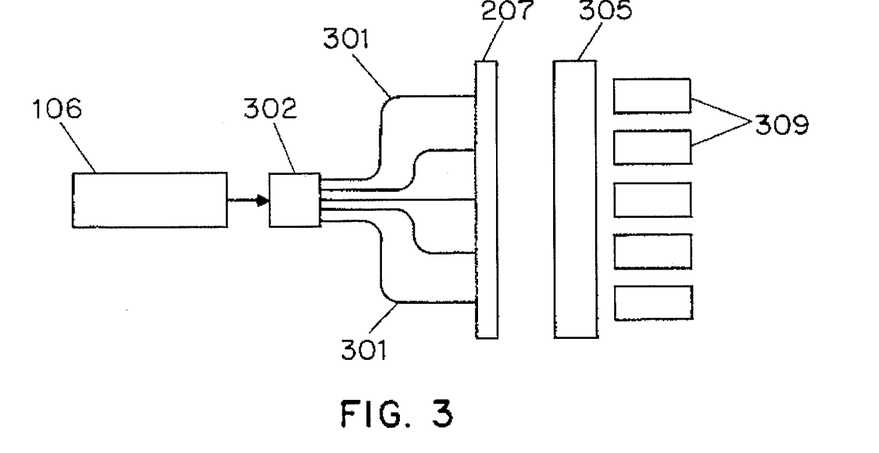
FIG. 3 shows a top sectional view of an embodiment of the invention.

In FIG. 2, delivery of the polarized incident radiation beam to the elongated detection zone 205 is accomplished using a radiation source 106, spherical lens 202 to broaden the beam into a wide angle beam and a cylindrical lens 206 which produces a narrow elongated line of light. A polarizing filter 207 permits light of one plane of polarization to pass through to the detection zone 205. Exiting light is filtered through a second polarization filter 208, and any transmitted light is detected by detectors 209. It will be appreciated, however, that other means for delivering the radiation to the elongated detection zone may be used. For example, the radiation my be delivered from the source 106 to a linear array of detection sites, making up an elongated detection zone 305 within the gel, using an array of optical fibers 301 and an optical coupler 302 as shown in FIG. 3. The polarization filter 207 or comparable optical component is disposed between the ends of the optical fibers 301 and the detection zone 305. In addition, the second polarization filter may be a single unit with the detector 309 as shown. Individual radiation sources 409, particularly LED's, and individual polarizing filters 407 may also be used for each of the detection sites in such an array as shown in FIG. 4.

Figure 4:
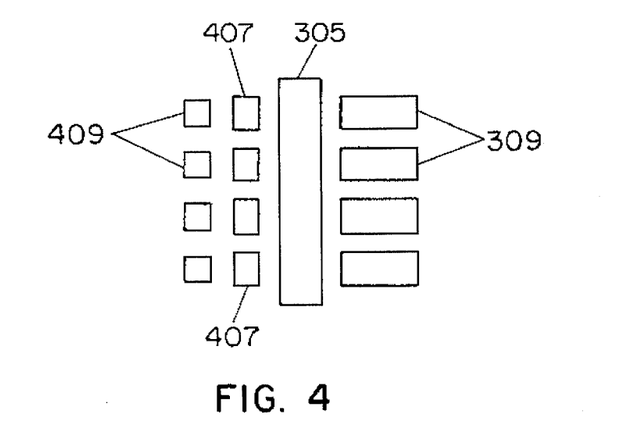
FIG. 4 shows a top sectional view of a further embodiment of the invention.
Figure 5:
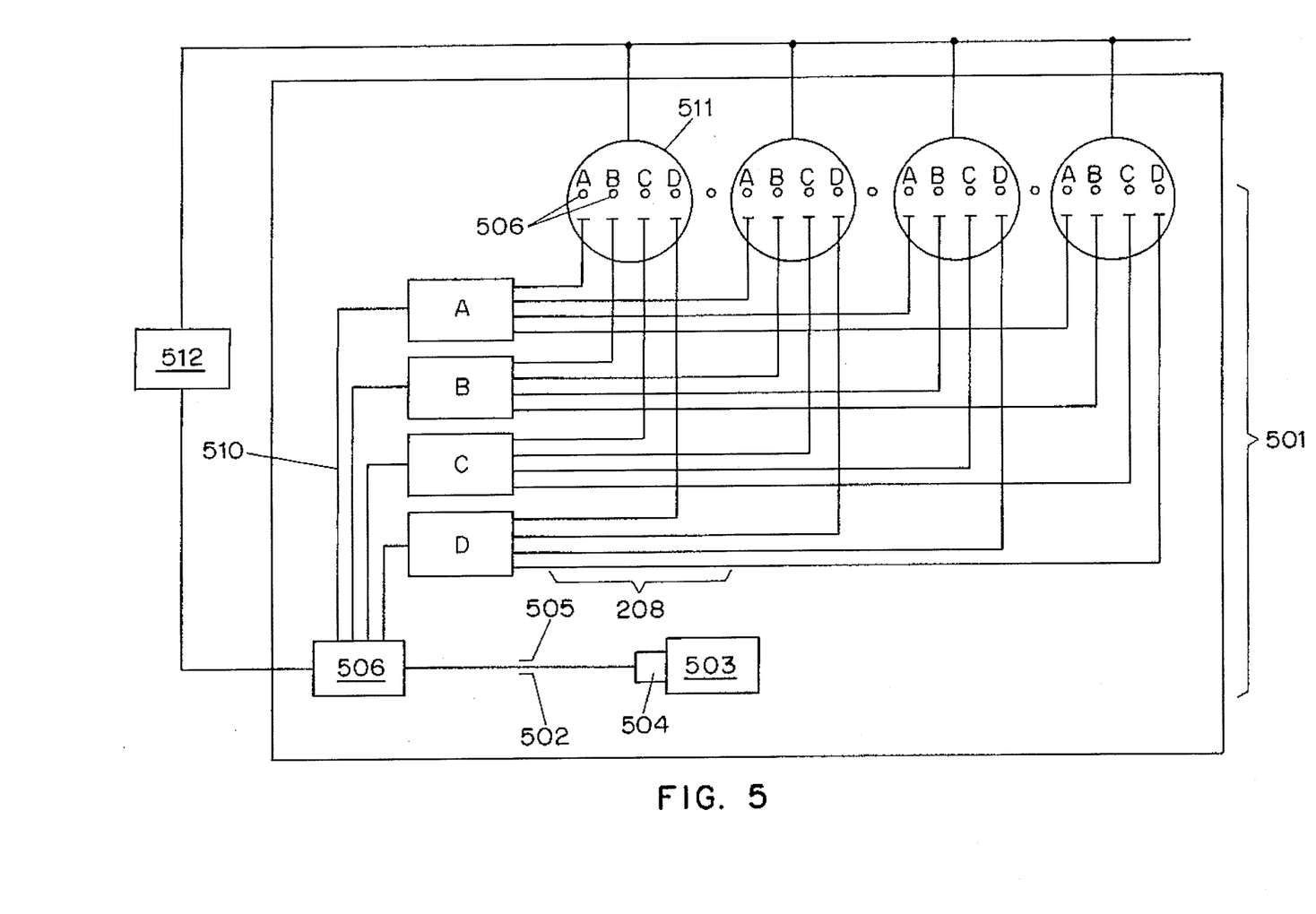
FIG. 5 shows a further embodiment of the invention.

In the embodiments shown in FIGS. 2–4, each of the detection sites within the elongated detection zone are irradiated concurrently. In some cases, however, the detection sites may be so close together that radiation from one detection site is collected at the adjacent site, leading to a loss of accuracy. In this case, it may be advantageous to divide the detection sites into two or more sets, and monitor the sets one at a time for the presence of optically active molecules within the detection sites. FIG. 5 shows an apparatus which can be used for this purpose.

As shown in FIG. 5, the incident radiation beam is conveyed to the excitation site by a fixed multiplexed fiber optic array, 501. Radiation, 502, from a source such as a laser or radiation emitting diode, 503, is coupled, using a fiber launch or the like, 504, into an optical fiber 505. The optical fiber carries the beam to a miniature board mountable switch, 506, that permits the switching of an optical signal from one output fiber 510 to another. For example, optical switching can be accomplished using a switch available from AMP, Inc., Harrisburg, Pa., in which a slight pivoting motion of a spherical mirror reflects the optical signal into one of two output fibers. The switch takes approximately 5–10 milliseconds to settle after each change. Several switches can be used in combination permitting the excitation beam to be divided into any number of output optical fibers 510.

As shown in FIG. 5, four output fibers 510 are used to permit the sequential excitation of four groups of excitation/detection sites. The use of four output fibers is merely exemplary, however. In general, the apparatus of the invention will divide the incident radiation into from 2 to 10 groups.

Radiation in each output fiber 510 is conducted by the output optical fiber 510 to a beam splitter 507A, 507B, 507C or 507D which separates the beam into a plurality of final optical fibers 508, each conducting its respective fraction of the input excitation beam as an excitation beamlet. Each of the split optical fibers conveys the beamlet through a polarizing filter 509 from which the beamlet exits to irradiate its respective detection site, 506. There may be one polarizing filter for each detection site, or a single elongated filter extending across the entire detection zone.

The final optical fibers 508 and the filter 509 are disposed to form a linear array of detection sites within an elongated detection zone. Within this array, the final optical fibers 508 are ordered so that, when using four groups of excitation signals, every fourth detection site belongs to the same group. The effect is that only a sub-set of excitation sites are irradiated at any one time (A, B, C, or D). Of course, if one were using two groups of excitation signals (only a single split of the incident beam 502), the final optical fibers 508 would be arranged in an alternating pattern. This provides the advantage that a single detector, 511, may be employed to detect changes in polarization from a plurality of detection sites if the detector output is synchronized with the switch so as to allow the signal processor to identify which signal came from which detection site.

The optical switch, 506, is programmed to switch the input laser beam into each of the output fibers 510 (and thus into the final optical fibers 508), for a period of preferably 20–100 milliseconds. Synchronization of the switch and detectors may be obtained with a microprocessor, 512.

The fixed multiplexed fiber optic array permits a high number of data points per second to be taken from each lane of the gel by conveying pulsed irradiation to each detection site. Further, it permits use of a reduced number of detectors.

Figure 6:
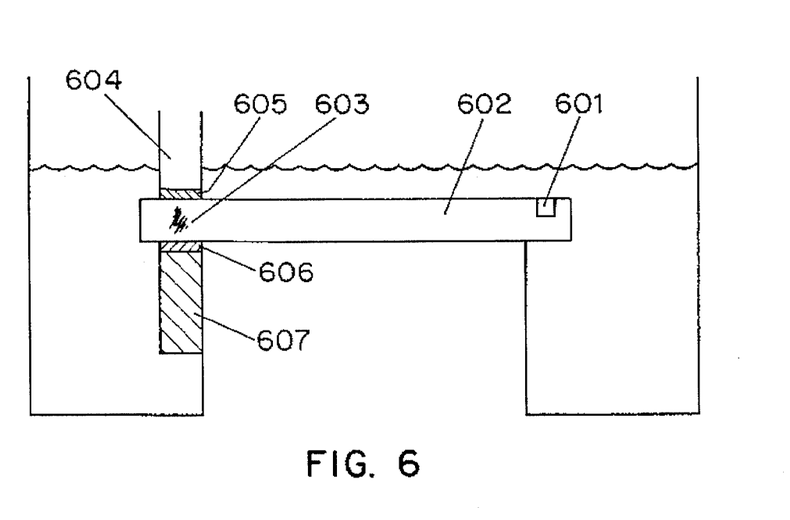
FIG. 6 is a view of the invention when applied for use in submarine agarose gel electrophoresis.

FIG. 6 illustrates an embodiment of the invention for use in thick agarose submarine gels. Sample is loaded at the loading site 601 of an agarose gel 602. Migration of the sample through the gel 602 under electrophoresis is detected at a detecting zone 603. The input radiation source 604 emits radiation of a plurality of polarities that is filtered to a unique polarity by a first polarizing filter 605 and directed at the detection zone 603. If a band of molecules is present it will shift the polarity of the radiation, thus permitting or preventing transmission (based on the orientation of the second polarizing filter 706) of radiation to the detector 607. Apparatus of this type are particularly suited to the rapid analysis of plasmids and DNA fragments of 30–10,000 nucleotides in length.

Figure 7:
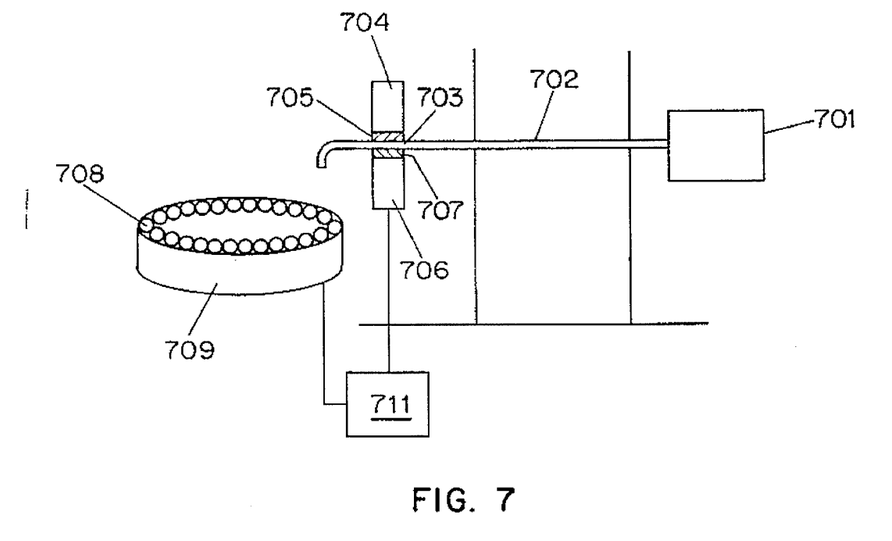
FIG. 7 is a view of the invention when applied for use with a capillary separation and collection column.

FIG. 7 illustrates use of the invention for collection of specific bands of molecules which have been separated on a separation matrix. Sample loaded in the source of a separation tube 701 flows along a separation capillary 702. Incident radiation from radiation source 704 and first polarizing filter 705 impinges on detection zone 703. The presence or absence of a group of optically active molecules is identified by the detector 706 after transmission through a second polarization filter 707, and reported to the user or to a microprocessor system controller 711 in real time. The microprocessor 711 controls a receiving tray 709 containing a plurality of vessels 708, and causes the tray to rotate to bring a new vessel into alignment with the outlet of the separation capillary 702 in response to changes in the intensity of the radiation received by the detector 706. In general, as is known in the art relating to automatic sample collection apparatus, the rotation of the tray is triggered by the rate of change of the detector output.

We claim:

1. A method for separating and detecting the presence of optically active molecules within a detection zone located within a separation matrix comprising the steps of:

(a) loading at least one sample containing optically active molecules onto a separation matrix having a detection zone located within the separation matrix;

(b) applying a motive force to the loaded sample to cause the loaded sample to migrate through the separation matrix and to separate the loaded sample into a plurality of subgroups of optically active molecules;

(c) directing an incident beam of polarized radiation to the detection zone within the separation matrix;

(d) processing an exiting beam of radiation which has passed through the detection zone within the separation matrix with an optical component which discriminates between radiation having the same polarization as the incident beam and radiation having a different polarization from the incident beam; and (e) measuring the intensity of the processed exiting beam, wherein a difference between the intensity of the filtered exiting beam and a standard intensity obtained for the separation matrix in the absence of sample is indicative of the presence of an optically active molecule in the detection zone.

2. A method according to claim 1, wherein the sample contains nucleic acid polymers.

3. A method according to claim 1, wherein the sample contains polypeptides or proteins.

4. A method according to claim 1, wherein motive force is an electric field applied to the separation matrix.

5. A method according to claim 4, wherein the separation matrix is a polyacrylamide gel.

6. A method according to claim 1, wherein a plurality of samples are loaded onto a single separation matrix in parallel lanes.

7. A method according to claim 6, wherein the plurality of samples each contains nucleic acid polymers.

8. A method according to claim 7, wherein the plurality of samples are products of a chain termination sequencing reaction.

9. A method according to claim 1, wherein the incident beam of polarized radiation is plane polarized.

10. A method according to claim 1, wherein the radiation is ultraviolet light.

11. A method according to claim 1, wherein the radiation is near infrared radiation.

12. A method according to claim 1, wherein the detection of optically active molecules is carried out in real-time during the separation of the molecules on the separation matrix.

13. A method according to claim 1, wherein the incident beam is elliptically polarized radiation having a major vector and a less intense minor vector.

14. A method according to claim 13, wherein radiation of the minor vector is detected in the absence of optically active molecules in the detection zone, and radiation of the major vector is detected when optically active molecules are present in the detection zone.

15. A method according to claim 1, further comprising the step of inducing formation of bifringent liquid crystals of the optically active molecules within the detection zone, wherein rotation of polarized light by said liquid crytsals is detected.

16. An apparatus for detection of optically active molecules in a separation matrix, comprising (a) a source of polarized radiation;

(b) a separation matrix having a detection zone disposed within the separation matrix and extending perpendicular to the direction of sample migration within the separation matrix, said separation matrix being disposed in a position such that the detection zone is in the path of the polarized radiation;

(c) an optical component which discriminates between polarized radiation which has passed through the detection zone within the separation matrix in the absence of optically active molecules and polarized radiation which has passed through the detection zone within the separation matrix in the presence of optically active molecules from the sample; and (d) at least one detector for determining the variations in the intensity of the radiation which passes through the optical component.

17. An apparatus according to claim 16, wherein the optical component is a polarization filter.

18. An apparatus according to claim 16, wherein the radiation source is a laser and the output of the laser is passed through a second optical component to produce a polarized beam of radiation.

19. An apparatus according to claim 16, wherein the radiation source is a radiation emitting diode and the output of the light emitting diode is passed through a second optical component to produce a polarized beam of radiation.

20. An apparatus according to claim 16, wherein the detector is a photomultiplier tube.

21. An apparatus according to claim 16, wherein the detector is a silicon photodiode.

22. An apparatus according to claim 16, further comprising means for applying a motive force to the separation matrix.

23. An apparatus according to claim 22, wherein the means for applying a motive force comprises first and second electrodes disposed at opposing ends of the separation matrix whereby an electric filed may be induced within the separation matrix.

24. An apparatus according to claim 16, wherein the detection zone comprises a linear array of detection sites, and comprising a plurality of detectors aligned with the detection sites.

25. An apparatus according to claim 24, wherein the radiation source comprises a plurality of light emitting diodes disposed in alignment with the linear array of detection sites.

26. An apparatus according to claim 24, further comprising means for sequentially delivering radiation from the radiation source to each of a plurality of pre-defined groups of detection sites within the detection zone.

27. An apparatus according to claim 26, wherein the radiation source is a laser.

28. An apparatus according to claim 16, wherein the source of polarized radiation produces elliptically polarized radiation.

29. An apparatus according to claim 16, further comprising means for applying a localized high density pulsed electric field to the detection zone.

30. An apparatus for detection of optically active molecules in a separation matrix, comprising (a) a source of alternatingly left and right circularly polarized radiation;

(b) a separation matrix having a detection zone disposed within the separation matrix and extending perpendicular to the direction of sample migration within the separation matrix, said separation matrix being disposed in a position relative to the source of polarized radiation such that the detection zone is in the path of polarized radiation from the source; and (c) a detector for determining the intensity of the radiation which has passed through the detection zone within the separation matrix.

31. An apparatus according to claim 30, wherein the source of polarized radiation is a Pockels cell or Ker cell.

32. An apparatus according to claim 30, further comprising means for applying an electromotive force to separate charged molecules within the separation matrix.

33. An apparatus for detection of optically active molecules in a separation matrix, comprising (a) a source of polarized radiation;

(b) a separation matrix disposed in a position such that a detection zone within the separation matrix is in the path of the polarized radiation;

(c) means for applying an electromotive force to separate charged molecules within the separation matrix;

(d) an optical component which discriminates between polarized radiation which has passed through the separation matrix in the absence of optically active molecules and polarized radiation which has passed through the separation matrix in the presence of optically active molecules from the sample; and (e) a detector for determining the intensity of the radiation which passes through the filter.

34. An apparatus according to claim 33, wherein the means for applying an electromotive force comprises first and second electrodes disposed at opposing ends of the separation matrix whereby an electric filed may be induced within the separation matrix.

35. A method for separating and detecting the presence of optically active molecules within a detection zone in a separation matrix comprising the steps of:

(a) loading a sample containing optically active molecules onto a separation matrix having a detection zone disposed within the separation matrix;

(b) applying a motive force to the loaded sample to cause the loaded sample to migrate through the separation matrix and to separate the sample into a plurality of subgroups of optically active molecules;

(c) directing an incident beam of alternating left and right circularly polarized radiation to the detection zone within the separation matrix;

(d) collecting an exiting beam of radiation which has passed through the detection zone within the separation matrix; and (e) monitoring the intensity of the exiting beam, wherein a difference between the intensity of the exiting beam and a standard intensity obtained for the separation matrix in the absence of sample is indicative of the presence of an optically active molecule in the detection zone.

36. An apparatus for detection of optically active molecules in a separation matrix, comprising (a) a source of alternatingly left and right circularly polarized radiation;

(b) a separation matrix disposed in a position such that a detection zone within the separation matrix is in the path of the polarized radiation;

(c) means for applying an electromotive force to separate charged molecules within the separation matrix; and (d) a detector for determining the intensity of the radiation which has passed through the detection zone of the separation matrix.

37. An apparatus according to claim 36, wherein the source of circularly polarized light comprises a Pockels cell or Ker cell.

38. A method for detecting nucleic acid polymers distributed within a gel comprising the steps of:

(a) directing an incident beam of polarized radiation at the gel containing the nucleic acid polymers;

(b) collecting radiation which has passed through the gel; and (c) analyzing the collected radiation for variations in polarization.

39. A method for sequencing nucleic acid polymers comprising the steps of:

(a) preparing a sequencing product mixture;

(b) loading the sequencing product mixture onto a loading site near a first end of an electrophoresis gel;

(c) applying an electric field to the gel to cause molecules loaded onto the gel to migrate from the loading site towards a detection site located at an opposing end of the gel;

(d) directing a beam of polarized radiation to the detection site and collecting radiation which has passed through the detection site; and (e) evaluating the collected radiation for changes in polarization, wherein changes in polarization reflect the presence of oligonucleotide fragments within the detection site.

40. A method according to claim 39, wherein a plurality of sequencing product mixtures are prepared and loaded onto adjacent loading sites of a single gel, and wherein polarized radiation is directed to a plurality of detection sites.

41. A method according to claim 39, wherein the beam of polarized radiation is alternately left and right circularly polarized, and the collected radiation is evaluated for preferential absorption of left or right circularly polarized radiation.

42. A method according to claim 39, wherein the beam of polarized radiation is plane polarized, and the collected radiation is evaluated for changes in polarization angle.

43. A method according to claim 39, wherein the beam of polarized radiation is elliptically polarized radiation having a major vector and a less intense minor vector, and the collected radiation is evaluated to detect the minor vector in the absence of oligonucleotide fragments in the detection zone, and the major vector in the presence of oligonucleotide fragments in the detection zone.

\* \* \* \* \*

Disclaimer 5,543,018 - John K. Stevens; Alexandre M. Ismailov, both of Toronto, Canada. METHOD AND APPARATUS FOR AUTOMATED ELECTROPHORESIS USING LIGHT POLARIZATION DETECTOR. Patent dated Aug. 6, 1996. Disclaimer filed Apr. 21, 1999, by the assignee, Visible Genetics Inc.

Hereby enters this disclaimer to claims 1-11, 16-23, 28, 33, 34, 38-40, and 42.

*(Official Gazette, June 22, 1999)*